United States Patent [19]
Darouiche

[11] Patent Number: 6,162,487
[45] Date of Patent: *Dec. 19, 2000

[54] METHOD OF COATING MEDICAL DEVICES WITH A COMBINATION OF ANTISEPTICS AND ANTISEPTIC COATING THEREFOR

[75] Inventor: Rabih O. Darouiche, Houston, Tex.

[73] Assignee: Baylor College of Medicine, Houston, Tex.

[*] Notice: This patent is subject to a terminal disclaimer.

[21] Appl. No.: 08/824,980

[22] Filed: Mar. 27, 1997

Related U.S. Application Data

[62] Division of application No. 08/555,198, Nov. 8, 1995.

[51] Int. Cl.[7] .................. C08J 7/02; B05D 1/34
[52] U.S. Cl. .............. 427/2.14; 427/2.24; 427/2.3; 424/423; 424/425; 424/484; 604/265; 623/901
[58] Field of Search .................. 424/422, 423, 424/425; 427/2.14, 2.22, 2.24, 2.3; 604/265; 623/901

[56] References Cited

U.S. PATENT DOCUMENTS

| | | | |
|---|---|---|---|
| 3,699,956 | 10/1972 | Kitrilakis et al. | 604/175 |
| 4,539,234 | 9/1985 | Sakamoto et al. | 427/393.5 |
| 4,605,564 | 8/1986 | Kulla et al. | 427/2.3 |
| 4,723,950 | 2/1988 | Lee | 604/322 |
| 5,019,096 | 5/1991 | Fox, Jr. et al. | 623/1 |
| 5,069,899 | 12/1991 | Whitbourne et al. | 424/56 |
| 5,217,493 | 6/1993 | Raad et al. | 623/11 |
| 5,335,373 | 8/1994 | Dangman et al. | 2/161.7 |
| 5,525,348 | 6/1996 | Whitbourne et al. | 424/423 |
| 5,624,704 | 4/1997 | Darouiche et al. | 427/2.24 |
| 5,674,513 | 10/1997 | Snyder, Jr. et al. | 424/404 |
| 5,688,516 | 11/1997 | Raad et al. | 424/409 |
| 5,756,145 | 5/1998 | Darouiche | 427/2.24 |
| 5,853,745 | 12/1998 | Darouiche | 424/423 |
| 5,902,283 | 5/1999 | Darouiche et al. | 604/265 |

FOREIGN PATENT DOCUMENTS

| | | |
|---|---|---|
| 60-36064 | 2/1985 | Japan . |
| 87/03495 | 6/1987 | WIPO . |

*Primary Examiner*—Robert H. Harrison
*Attorney, Agent, or Firm*—Fulbright & Jaworski L.L.P.; Thomas D. Paul

[57] ABSTRACT

A medical device of metallic or non-metallic material coated with a combination of antiseptics and a method for coating such an implant with a combination of antiseptics is provided. Different combinations of antiseptics can be used for different types of medical devices depending on the spectrum of organisms that cause the infections related to each device. The combination of different antiseptics has a synergistic effect against certain bacteria and fungi. The combination of antiseptic can be applied to the surface of a metallic device by dissolving the combination of antiseptics and a polymeric sticking agent in an acid solution to form an antiseptic solution, and applying the antiseptic solution, in an effective concentration to inhibit the growth of bacterial and fungal organisms, to at least a portion of the surfaces of the medical device. The antiseptic combination can be applied to the surface of and impregnate the material of a non-metallic implant by forming an antiseptic composition by dissolving the combination of antiseptics in an organic solvent and adding a penetrating agent to the composition, and applying the antiseptic composition to at least a portion of the medical implant under conditions where the antiseptic composition permeates the material of the medical implant.

11 Claims, No Drawings

METHOD OF COATING MEDICAL DEVICES WITH A COMBINATION OF ANTISEPTICS AND ANTISEPTIC COATING THEREFOR

This is a division of application Ser. No. 08/555,198 filed Nov. 8, 1995.

BACKGROUND OF THE INVENTION

1. Field of the Invention

The present invention relates to the use of a combination of antiseptics for coating or impregnating indwelling or implanted medical devices, to inhibit the growth of bacterial and fungal organisms. The invention also relates to a method of coating or impregnating the indwelling or implanted medical device with a combination of antiseptics.

2. Description of the Prior Art

Indwelling vascular catheters are becoming essential in the management of hospitalized patients. Implanted orthopedic devices are also becoming more prevalent, partly to meet the needs of a growing elderly population. The benefit derived from these catheters and orthopedic devices, as well as other types of medical implants is often offset by infectious complications. The most common organisms causing infectious complications of vascular catheters and orthopedic devices are *Staphylococcus epidermidis* and *Staphylococcus aureus*. In the case of vascular catheters, these two organisms account for almost 70–80% of all infectious organisms, with Staphylococcus epidermidis being the most common organism. Gram-negative bacilli cause about 15–20% of infected cases, and Candida species, a fungal agent, accounts for about 10–15% of vascular catheter infections. *Staphylococcus epidermidis* and *Staphylococcus aureus* also are responsible for about two-thirds of the cases of infection in orthopedic implants. Other gram-negative bacteria and fungal organisms (Candida) account for the remaining one-third of cases.

Another common hospital-acquired infection is urinary tract infection (UTI). The majority of cases of UTI are associated with the use of urinary catheters, including transurethral foley, suprapubic and nephrostomy catheters. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTI continues to pose a major problem. In the U.S. alone, about 1 million cases of hospital-acquired cases of UTI occur annually. For instance, it is estimated that almost one-quarter of hospitalized spinal cord-injured patients develop symptomatic UTI during their hospital course. Gram-negative bacilli account for almost 60–70%, enterococci for about 25% and Candida species for about 10% of cases of UTI.

Colonization of bacteria on the surfaces of the implant or other parts of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices. In such attempts the objective has been to produce a sufficient bacteriostatic or bactericidal action to prevent colonization.

Various methods have previously been employed to prevent infection of medical devices. One of the simplest methods would be to flush the surfaces of the device with an antibiotic solution. Generally, the flushing technique would require convenient access to the implantable device. For example, catheters are generally amenable to flushing with a solution of rifampin and minocycline or rifampin and novobiocin. For use in flushing solutions, the effective concentration of the antibiotic would range from about 1 to 10 mg/ml for minocycline, preferably about 2 mg/ml; 1 to 10 mg/ml for rifampin, preferably about 2 mg/ml; and 1 to 10 mg/ml for novobiocin, preferably about 2 mg/ml. The flushing solution would normally be composed of sterile water or sterile normal saline solutions.

A method of coating the devices would be to first apply or absorb to the surface of the medical device a layer of surfactant, such as tridodecylmethyl ammonium chloride (TDMAC) surfactant followed by an antibiotic coating layer. For example, a medical device having a polymeric surface, such as polyethylene, silastic elastomers, polytetrafluoroethylene or Dacron, can be soaked in a 5% by weight solution of TDMAC for 30 minutes at room temperature, air dried, and rinsed in water to remove excess TDMAC. Alternatively, TDMAC pre-coated central vascular catheters are commercially available. The device carrying the absorbed TDMAC surfactant coating can then be incubated in an antibiotic solution for up to one hour or so, allowed to dry, then washed in sterile water to remove unbound antibiotic and stored in a sterile package until ready for implantation. In general, the antibiotic solution is composed of a concentration of 0.01 mg/ml to 60 mg/ml of each antibiotic in an aqueous pH 7.4–7.6 buffered solution, sterile water, or methanol. According to one method, an antibiotic solution of 60 mg of minocycline and 30 mg of rifampin per ml of solution is applied to the TDMAC coated catheter.

A further method known to coat the surface of medical devices with antibiotics involves first coating the selected surfaces with benzalkonium chloride followed by ionic bonding of the antibiotic composition. See, e.g., Solomon, D. D. and Sherertz, R. J., *J. Controlled Release*, 6:343–352 (1987) and U.S. Pat. No. 4,442,133.

Other methods of coating surfaces of medical devices with antibiotics are taught in U.S. Pat. No. 4,895,566 (a medical device substrate carrying a negatively charged group having a pK of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods of coating medical devices with antibiotics appear in numerous patents and medical journal articles. However, although antibiotic-coated medical devices, such as those coated with minocycline and rifampin, are very effective against Staphylococci, their efficacy against gram-negative bacteria and candida is limited. Moreover, there exists a potential concern of developing antibiotic resistance due to the use of antibiotics for coating devices.

Accordingly, there is a need for an antimicrobial coated medical device that will provide a broader range of antimicrobial activity. There is also a need for an antimicrobial coated medical device that will avoid the potential concern of developing antibiotic resistance.

SUMMARY OF THE INVENTION

An object of the present invention is the provision of an antiseptic coated medical device.

A further object of the invention is a practical, inexpensive, safe and effective method for coating or impregnating medical devices with a combination of antiseptics.

Another object of the invention is the application of a combination of antiseptics to a medical device to avoid developing antibiotic resistance.

Thus in accomplishing the foregoing objects, there is provided in accordance with one aspect of the present invention an implantable medical device comprising a medical device having one or more surfaces; and an antiseptic composition layer coating said one or more surfaces of the medical device, the antiseptic composition including a combination of antiseptics in an effective concentration to inhibit the growth of bacterial and fungal organisms. The medical device can be either a metallic or a non-metallic device.

In the non-metallic embodiment the antiseptic composition layer penetrates the surfaces thereof. The antiseptic composition, according to this embodiment, may preferably comprise a mixture of the combination of antiseptics, an organic solvent, such as methanol, and a penetrating agent, such as butyl acetate. The combination of antiseptics include methylisothiazolone and α-terpineol; thymol and cetylpyridinium chloride; thymol and methylisothiazolone; or thymol and chloroxylenol. The medical device may be a urinary catheter, a vascular catheter, a vascular graft, a vascular catheter port, a wound drain tube, a hydrocephalus shunt, a peritoneal dialysis catheter, a pacemaker capsule, an artificial urinary sphincter, a small or temporary joint replacement, a urinary dilator, a long term urinary device, a tissue bonding urinary device, a penile prosthesis, a heart valve, or the like.

According to a further aspect of the invention, the antiseptic composition layer may further comprise a mixture of a polymeric sticking agent and an acid solution.

The metallic medical device embodiment is comprised of a metallic alloy, such as stainless steel, titanium, tivanium, vitallium, chromium alloy, cobalt alloy and combinations thereof. The medical device preferably comprises an orthopedic implant selected from the group consisting of joint prosthesis, screw, nail, nut, bolt, plate, rod, pin, wire, insertor, osteoport and halo device. The combination of antiseptics include chlorhexidine, methylisothiazolane and thymol; chlorhexidine and chloroxylenol; chlorhexidine and cetylpyridinium chloride.

A further embodiment of the invention provides a method for impregnating the non-metallic medical device with a combination of antiseptics comprising the steps of forming an effective concentration of an antiseptic composition to inhibit the growth of bacterial and fungal organisms by dissolving an effective concentration of the combination of antiseptics in an organic solvent and adding a penetrating agent to the composition; and applying the antiseptic composition to at least a portion of the medical device under conditions where the antiseptic composition permeates the material of the medical device.

The step of applying the antiseptic composition to the medical device may comprise dipping the device in the composition for a period of between about 15 to 120 minutes, preferably about 60 minutes, and removing the impregnated medical device from the antiseptic composition.

Still a further embodiment of the present invention provides a method for coating a medical device, such as an orthopedic implant, with a combination of antiseptics comprising the steps of dissolving the combination of antiseptics and a polymeric sticking agent in an acid solution to form an antiseptic solution; and applying said antiseptic solution, in an effective concentration to inhibit the growth of bacterial and fungal organisms, to at least a portion of the surfaces of said medical device. The device also may be allowed to dry after the antiseptic solution is applied to the surfaces thereof.

One aspect of this embodiment provides that the step of applying the antiseptic solution comprises dipping the device into the antiseptic solution for a period of approximately one minute; and the step of drying the device comprises drying the device for at least 4 hours.

The combination of antiseptics include chlorhexidine, methylisothiazolone and α-terpineol; chlorhexidine and cetylpyridinium chloride; chlorhexidine and chloroxylenol; chlorhexidine, methylisothiazolane and thymol; methylisothiazolone or thymol and chloroxylenol.

DETAILED DESCRIPTION

The term "antiseptics" as used in the present invention means any of a category of antimicrobial substances that inhibits the action of microorganisms, including but not limited to chlorhexidine, methylisothiazolone, thymol, α-terpineol, cetylpyridinium chloride and chloroxylenol.

Chlorhexidine (Chlorhexidine gluconate) is a biguanide with a very rapid bactericidal activity against a broad range of microorganisms, including gram-positive bacteria (such as staphylococci, Enterococcus species), gram-negative bacteria (such as *Escherichia coli* and *Pseudomonas aeruginosa*) and Candida species. Chlorhexidine causes disruption of microbial cell membranes and precipitation of cellular contents, and its effectiveness is not affected by the presence of organic matter, such as blood. An important attribute of chlorhexidine is its prolonged persistence on the skin, which is beneficial for reducing infections related to medical devices that are usually caused by organisms migrating from skin, such as vascular catheter and orthopedic device-related infections. Chlorhexidine is soluble in acetic acid and formic acid, but is generally not soluble in organic solvents. Chlorhexidine has been used extensively as a skin cleanser for over 20 years, and also has been used to coat vascular catheters either alone or in combination with silver sulfadiazine.

Methylisothiazolone (2-Methylisothiazolone Hydrochloride) is a bacteriostatic antiseptic with a broad spectrum antimicrobial activity against gram-positive bacteria (MIC for *Staphylococcus aureus*=80 µg/ml; MIC for Enterococcus species=80 µg/ml), gram-negative bacteria (MIC for *Escherichia coli* =40 µg/ml; MIC for *Pseudomonas aeruginosa*=80 µg/ml) and Candida species (MIC for *Candida albicans*=320 µg/ml). Methylisothiazolone is soluble in formic acid and organic solvents, but is not soluble in acetic acid. Methylisothiazolone has been used to prevent bacterial and algae growth in water cooling systems.

Thymol(5-methyl-2 isopropyl phenol) is a bacteriostatic antiseptic with a broad spectrum antimicrobial activity against gram-positive bacteria (such as staphylococci and Enterococcus species), gram-negative bacteria (such as *Escherichia coli* and *Pseudomonas aeruginosa*) and Candida species. Thymol is soluble in acetic acid and organic solvents, but is not soluble in formic acid. Thymol has been used in mouth wash preparations.

α-Terpineol (α-α-4-trimethyl-3-cyclohexine-1-methanol) is a bacteriostatic antiseptic that is chemically related to thymol and shares with thymol the same broad spectrum antimicrobial activity against gram-positive bacteria (such as staphylococci and Enterococcus species), gram-negative bacteria (such as *Escherichia coli* and *Pseudomonas aeruginosa*) and Candida species. α-Terpineol is soluble in acetic acid and organic solvents, but is not soluble in formic acid. α-terpineol has been used in mouth wash preparations.

Cetylpyridinium chloride (1-Hexadecylpyridinium chloride) is an antiseptic which has activity against gram-positive bacteria and Candida. It has been used in mouth lozenges (as in "Cepacol") and in antiseptive cream, tincture, and solution preparations (as in "Fungoid").

Chloroxylenol (4-chloro, 3,5-dimethyl phenol) is an antiseptic which has shown good antimicrobial activity against gram-positive bacteria and fungi, and fair activity against gram-negative bacteria. It has been used in antimicrobial soap solution (as in "Ultradex"), antiseptic creme, tincture and solution preparations (as in "Fungoid"). Its effectiveness is minimally affected by organic matter, and persists in skin for a few hours.

These antiseptics are preferably used in combinations of two or more of them to obtain a synergistic effect. The antiseptic combination provides a broader range of antimicrobial activity than antibiotic coatings. They are dispersed along the surface of the medical device.

Some examples of combinations of antiseptics include a mixture of chlorhexidine, methylisothiazolone and α-terpineol; thymol and chloroxylenol; thymol and methylisothiazolone; chlorhexidine and cetylpyridinium chloride; chlorhexidine and chloroxylenol; or chlorhexidine, methylisothiazolone and thymol. These combinations provide a broad spectrum of activity against a wide variety of organisms.

The amount of each antiseptic agent used to coat the medical device varies to some extent, but is at least a sufficient amount to form an effective concentration to inhibit the growth of bacterial and fungal organisms, such as staphylococci, gram-positive bacteria, gram-negative bacilli and Candida.

The term "effective concentration" means that a sufficient amount of the antiseptic agent is added to decrease, prevent or inhibit the growth of bacterial and/or fungal organisms. The amount will vary for each compound and upon known factors such as pharmaceutical characteristics; the type of medical device; age, sex, health and weight of the recipient; and the use and length of use. It is within the skilled artisan's ability to relatively easily determine an effective concentration for each compound.

The term "organic solvent" as used in the present invention means solvents that can be used to dissolve antiseptic agents, including alcohols (i.e. methanol, ethanol), ketones (acetone, methylethylketone), ethers (tetrahydrofuran), aldehydes (formaldehyde), acetonitrile, glacial acetic acid, formic acid, methylene chloride and chloroform.

The term "penetrating agent" as used in the present invention means an organic compound that can be used to promote penetration of the antiseptic agent into the material of the medical device. Examples of these organic compounds are esters (i.e. ethyl acetate, propyl acetate, butyl acetate, amyl acetate, and combinations thereof), ketones (i.e. acetone and methylethylketone), methylene chloride and chloroform.

The term "polymeric sticking agent" as used in the present invention means any of a group of polymeric materials that can be used to coat the surface of a medical device. Examples of such polymeric materials are "polyvinyl" (as defined below), collodion (as defined below), polycarboxylic acids (i.e. polyacrylic acid, polymethacrylic acid, polymaleic acid, poly-(maleic acid monoester), polyaspartic acid, polyglutamic acid, aginic acid or pectimic acid), polycarboxylic acid anhydrides (i.e. polymaleic anhydride, polymethacrylic anhydride or polyacrylic acid anhydride), polyamines, polyamine ions (i.e. polyethylene imine, polyvinylamine, polylysine, poly-(dialkylamineoethyl methacrylate), poly-(dialkylaminomethyl styrene) or poly-(vinylpyridine)), polyammonium ions (i.e. poly-(2-methacryloxyethyl trialkyl ammonium ion), poly-(vinylbenzyl trialkyl ammonium ion), poly-(N,N,-alkylpyridinium ion) or poly-(dialkyloctamethylene ammonium ion) and polysulfonates (i.e. poly-(vinyl sulfonate) or poly-(styrene sulfonate)). Linear copolymers, crosslinked copolymers, graft polymers and block copolymers containing the monomers as constituents of the above exemplified polymers can also be used. These and other useful polymeric materials are listed in Sakamoto et al., U.S. Pat. No. 4,642,104, and are herein incorporated by reference.

The term "polyvinyl" as used in the present invention means any of a group of polymerized vinyl compounds such as PV-coA-coA (Polyvinyl butyryl-co-vinyl alcohol-co-vinylacetate), PV-coA-coA plus hydroxylapatite, PVP (Polyvinyl pyrrolidone), PVP-coVA (Polyvinyl pyrrolidone co-vinyl acetate dissolved in 2-propanol) and combinations thereof.

The term "bacterial and fungal organisms" as used in the present invention means all genuses and species of bacteria and fungi, including but not limited to all spherical, rod-shaped and spiral organisms. One skilled in the art recognizes that a variety of source books which list and describe bacteria and fungi are available, for example in the textbook "Principles and Practice of Infectious Diseases", Mandell et al., 4th edition, 1995, Churchill Livingstone, N.Y. Some examples of bacteria are staphylococci (i.e. *Staphylococcus epidermidis, Staphylococcus aureus*), *Enterococcus faecalis, Pseudomonas aeruginosa, Escherichia coli*, other gram-positive bacteria and gram-negative bacilli. One example of a fungus is *Candida albicans*.

As used herein "implanted" devices includes both temporary and permanent devices and indwelling and implanted devices.

The medical devices which are amenable to coating by the antiseptic combinations are generally composed of either metallic or non-metallic material.

Examples of metallic materials that can be coated by the method of the present invention are metallic alloys, such as stainless steel, titanium, tivanium, vitallium, chromium alloy, cobalt alloy and the like. Particular metallic devices especially suited for application of the antimicrobial combinations of this invention include orthopedic implants such as joint prostheses, screws, nails, nuts, bolts, plates, rods, pins, wires, inserters, osteoports, halo systems and other orthopedic devices used for stabilization or fixation of spinal and long bone fractures or disarticulations. Other metallic devices may include non-orthopedic devices such as tracheostomy devices, intraurethral and other genitourinary implants, stylets, dilators, stints, wire guides and access ports of subcutaneously implanted vascular catheters.

The non-metallic devices generally may be impregnated with the antimicrobial agents. Examples of non-metallic materials that can be coated by the method of the present invention include rubber, plastic, silicone, polyurethane, polyethylene, Gortex (polytetrafluoroethylene), Dacron (polyethylene tetraphthalate), Teflon (polytetrafluoroethylene), latex, elastomers and Dacron sealed with gelatin, collagen or albumin.

Particular non-metallic devices suited for application of the antimicrobial coating of the present invention include peripherally insertable central venous catheters, dialysis catheters, long term tunneled central venous catheters, peripheral venous catheters, short-term central venous catheters, arterial catheters, pulmonary artery Swan-Ganz catheters, urinary catheters, long term urinary devices, tissue bonding urinary devices, penile prostheses, vascular grafts, vascular catheter ports, wound drain tubes, hydrocephalus shunts, peritoneal catheters, pacemaker capsules, artificial urinary sphincters, small joint replacements, temporary joint replacements, urinary dilators, heart valves and the like.

In addition to antimicrobial coating of metallic and non-metallic medical implants, the antiseptics described in this invention can be potentially used to coat miscellaneous surfaces, such as hospital floors, nursing counters, counters adjacent to washing basins, desks, etc. to decrease transmission of hospital antibiotic-resistant microbial flora, such as methicillin-resistant *staphylococcus aureus*, vancomycin-resistant enterococci and antibiotic-resistant gram negative bacteria on the skin of health care personnel and patients. Another potential application would be the antimicrobial coating of kitchen counters to decrease transmission of organisms that cause food-borne poisoning, such as Salmonella species and *Escherichia coli*.

The present invention is directed primarily to an implantable medical device comprising a medical device having one or more surfaces; and an antiseptic composition layer coating said one or more surfaces of the medical device, the antiseptic composition includes a combination of antiseptics in an effective concentration to inhibit the growth of bacterial and fungal organisms. The use of antiseptics provides much improved efficacy against gram-negative bacteria and Candida species. Although the different mixtures of antiseptics can be used for all medical devices, certain mixtures work better with different devices. The different combinations of antiseptics are used for different types of medical devices depending on the spectrum of organisms that cause the infections related to each device. For instance, preferred combinations for coating orthopedic devices include chlorhexidine, methylisothiazolone and α-terpineol; chlorhexidine and cetylpyridinium chloride; chlorhexidine and chloroxylenol; or chlorhexidine, methylisothiazolane and thymol. For silicone urinary catheters, the preferred coating combination is thymol and methylisothiazolone or thymol and chloroxylenol. The combination of different antiseptics has a synergistic effect against certain bacteria and fungi.

According to a one embodiment of the invention, the medical device is a non-metallic device. The antiseptic composition layer penetrates the surfaces of the device and impregnates the device material. The antiseptic composition, according to one embodiment, preferably comprises a mixture of methylisothiazolone and thymol dissolved in a solution of methanol and butyl acetate.

The non-metallic medical device is impregnated with the combination of antiseptics by applying a sufficient amount of an antiseptic composition to at least a portion of the medical device under conditions where the antiseptic composition permeates the material of the medical device. The antiseptic composition is formed of an effective concentration to inhibit the growth of bacterial and fungal organisms by dissolving sufficient amounts of the mixture of antiseptics. In one specific embodiment, chloroxylenol and thymol were dissolved in a solution of methanol and butyl acetate. The step of applying the antiseptic composition to the medical device may comprise dipping the device in the composition for a period of between about 15 and 120 minutes, preferably about 60 minutes, and removing the impregnated medical device from the antiseptic composition.

According to another embodiment of the invention, the antiseptic composition layer comprises a mixture of a combination of antiseptics, a polymeric sticking agent and an acid solution. The preferred antiseptic combination according to the second embodiment comprises a mixture of chlorhexidine, methylisothiazolone and α-terpineol. The polymeric sticking agent is preferably polyvinyl butyryl-co-vinyl alcohol co-vinyl acetate, and the acid solution is a mixture of glacial acetic acid and formic acid. The medical device according to this aspect of the invention, is preferably comprised of a metallic alloy.

The medical device according to this embodiment is formed by applying an antiseptic solution, in an effective concentration to inhibit the growth of bacterial and fungal organisms, to at least a portion of the surfaces of the medical device. The device also may be allowed to dry after the antiseptic solution is applied to the surfaces thereof. The antiseptic solution is formed by dissolving a combination of antiseptics and a polymeric sticking agent in an acid solution to form an antiseptic solution. Preferably a mixture of chlorhexidine, methylisothiazolone and α-terpineol, and polyvinyl butyryl-co-vinyl alcohol co-vinyl acetate are dissolved in a solution of formic acid and glacial acetic acid to form the antiseptic solution. According to one preferred method, the step of applying the antiseptic solution comprises dipping the device into the antiseptic solution for a period of approximately one minute; and the step of drying the device for at least about 4 hours.

The following examples are offered by way of illustration and are not intended to limit the invention in any manner.

EXAMPLE 1

SYNERGY OF THE ANTISEPTIC COMBINATION WHEN USED FOR COATING OF MEDICAL DEVICES

A first antiseptic solution was formed by dissolving polyvinyl butyryl-co-vinyl alcohol-co-vinyl acetate (PV-coVA-coVA; 85 mg/ml) mixed with chlorhexidine (120 mg/ml) in an acid solution (50:50 glacial acetic acid and formic acid). A second antiseptic solution was formed by dissolving polyvinyl butyryl-co-vinyl alcohol-co-vinyl acetate (PV-coVA-coVA; 85 mg/ml) mixed with methylisothiazolone (60 mg/ml) in an acid solution (50:50 glacial acetic acid and formic acid). A third antiseptic solution was formed by dissolving polyvinyl butyryl-co-vinyl alcohol-co-vinyl acetate (PV-coVA-coVA; 85 mg/ml) mixed with thymol (20 mg/ml) in an acid solution (50:50 glacial acetic acid and formic acid). Finally, a fourth antiseptic solution was formed by dissolving polyvinyl butyryl-co-vinyl alcohol-co-vinyl acetate (PV-coVA-coVA; 85 mg/ml) and a mixture of chlorhexidine (120 mg/ml), methylisothiazolone (60 mg/ml) and thymol (20 mg/ml) in an acid solution (50:50 glacial acetic acid and formic acid).

Antiseptic coatings were applied to each of four stainless steel cylinders (0.5" diameter×2" length), using each of the above four antiseptic solutions, by dipping each cylinder for 1 minute at 50° C. in the respective solution. The coated cylinders were then allowed to dry for about 4 hours prior to being placed on agar plates that had been freshly overlaid with one of the microorganisms listed below in Table 1. After 18–24 hours of incubation at 37° C., the following measurements of zones of inhibition were taken.

TABLE 1

| | Zones of inhibition (m.m.) | | |
|---|---|---|---|
| Coating | Staph. epidermidis | Pseud. aeruginosa | Candida albicans |
| Chlorhexidine | 31 | 28 | 26 |
| Methylisothiazolone | 47 | 32 | 34 |
| Thymol | 23 | 18 | 14 |
| Combination of antiseptics | 52 | 44 | 43 |

These results show that the triple antiseptic combination of chlorhexidine, methylisothiazolone and thymol produces a synergistic effect against all tested organisms (i.e. zones of inhibition obtained with the triple combination were larger than zones of inhibition produced by each antiseptic alone).

EXAMPLE 2

COMPARISON OF RANGE OF ACTIVITY OF ANTISEPTIC VERSUS ANTIBIOTIC COATED ORTHOPEDIC DEVICES

An antibiotic solution was formed by dissolving polyvinyl butyryl-co-vinyl alcohol-co-vinyl acetate (PV-coVA-coVA; 70 mg/ml) mixed with an antibiotic combination (minocycline 50 mg/ml plus rifampin 50 mg/ml) in an acid solution (50:50 glacial acetic acid and formic acid). The antibiotic combination of minocycline and rifampin was selected for its proven broad spectrum of antimicrobial efficacy when used for coating of devices. An antiseptic solution was formed by dissolving polyvinyl butyryl-co-vinyl alcohol-co-vinyl acetate (PV-coVA-coVA; 85 mg/ml) mixed with an antiseptic combination (chlorhexidine 50 mg/ml plus methylisothiazolone 20 mg/ml plus α-terpineol 100 mg/ml) in an acid solution (50:50 glacial acetic acid and formic acid).

A triple-layer coating was applied to 0.5×2" stainless steel cylinders (diameter 12 mm). The triple layer coating was applied by first dipping a cylinder into either the antibiotic solution or the antiseptic solution for 1 minute at 50° C. After allowing the coated cylinders to dry for about 4 hours, each cylinder was dipped for just few seconds in collodion at room temperature. The cylinders were then allowed to dry for about 2 hours prior to dipping for just few seconds in a 50:50 solution of collodion and polycaprolactam (a form of nylon dissolved in formic acid at a concentration of 50 mg/ml; final concentration of caprolactam in coating solution being 25 mg/ml) at room temperature. Finally, the cylinders were allowed to dry for at least 2 hours, then were gas sterilized with ethylene oxide.

After 18–24 hours of incubation at 37° C. in agar plates that had been freshly overlaid with one of the microorganisms shown below in Table 2, the following measurements of zones of inhibition were recorded.

TABLE 2

| | Zones of inhibition (m.m.) | | |
|---|---|---|---|
| Coating | Staph. epidermidis | Pseud. aeroginosa | Candida albicans |
| Antibiotic combination | 37 | 25 | 25 |
| Antiseptic combination | 33 | 45 | 33 |

These results demonstrate that devices coated with the triple antiseptic combination of chlorhexidine, methylisothiazolone and α-terpineol (chemically related to thymol) have stronger activity against Pseudomonas aeruginosa and Candida albicans but have comparable activity against Staphylococcus epidermidis when compared with devices coated with the antibiotic combination of minocycline and rifampin.

EXAMPLE 3

COMPARISON OF RANGE OF ACTIVITY OF ANTISEPTIC VS. ANTIBIOTIC COATED CATHETERS

An antibiotic solution was formed containing 25 mg of minocycline and 40 mg of rifampin per ml of mixture of organic solvents (methanol plus butyl acetate, 15:85 volume ratio). The antibiotic combination of minocycline and rifampin was selected for its proven broad spectrum of antimicrobial efficacy when used for coating of devices. An antiseptic solution was formed containing methylisothiazolone 50 mg/ml plus thymol 150 mg/ml of mixture of organic solvents (methanol plus butyl acetate, 15:85 volume ratio).

18-french (diameter 4 mm) silicone urinary catheters were impregnated with either the antibiotic solution or the antiseptic combination by dipping the catheter in the respective solution for 60 minutes at 40° C.

TABLE 3

| | Zones of inhibition (m.m.) | | | |
|---|---|---|---|---|
| Coating | Enterococcus | E. coli | Pseud. aerugin | Candida albicans |
| Antibiotic combination | 29 | 29 | 17 | 19 |
| Antiseptic combination | 25 | 28 | 26 | 30 |

These results show that coating catheters with the antiseptic combination of methylisothiazolone and thymol is more protective against Pseudomonas aeruginosa and Candida albicans and is probably as protective against E. coli and enterococci when compared to the antibiotic combination of minocycline and rifampin.

EXAMPLE 4

SYNERGY OF ANTISEPTIC COATED ORTHOPEDIC DEVICES (SINGLE LAYER OF COATING)

A first antiseptic solution was formed by dissolving polyvinyl butyryl-co-vinyl alcohol-co-vinyl acetate (PV-coVA-coVA; 70 mg/ml) mixed with chlorhexidine (120 mg/ml) in an acid solution (50:50 glacial acetic acid and formic acid). A second antiseptic solution was formed by dissolving polyvinyl butyryl-co-vinyl alcohol-co-vinyl acetate (PV-coVA-coVA; 70 mg/ml) mixed with cetylpyridinium chloride (200 mg/ml) in an acid solution (50:50 glacial acetic acid and formic acid). A third antiseptic solution was formed by dissolving polyvinyl butyryl-co-vinyl alcohol-co-vinyl acetate (PV-coVA-coVA; 70 mg/ml) and a mixture of chlorhexidine (120 mg/ml), and cetylpyridinium chloride (200 mg/ml) in an acid solution (50:50 glacial acetic acid and formic acid).

Stainless steel cylinders (0.5×2") were dipped in one of the three antiseptic coating solutions for 1 minute at 50° C. Devices were allowed to dry for at least 4 hours, then placed into agar plates that had been freshly overlaid with one of the microorganisms shown below in Table 4. After 18–24 hours of incubation at 37° C., the following measurements of zones of inhibition were recorded.

TABLE 4

| Coating | Zones of inhibition (m.m.) | | |
|---|---|---|---|
| | S. epidermidis | P. aerug | Candida albicans |
| Chlorhexidine | 30 | 25 | 28 |
| Cetylpyridinium | 33 | 0 | 28 |
| Combination | >65 | 40 | >65 |

It is clear that the antiseptic combination of chlorhexidine and cetylpyridinium chloride was much better than either antiseptic alone and in all cases, better than the sum of antiseptics.

EXAMPLE 5

THYMOL AND CHLOROXYLENOL FOR COATING SILICONE URINARY CATHETERS

A first antiseptic solution was formed by dissolving chloroxylenol (200 mg/ml) in an 85:15 solution of butyl acetate: methanol that has NaOH (5 mg/ml of methanol). A second antiseptic solution was formed by dissolving thymol (150 mg/ml) in an 85:15 solution of butyl acetate: methanol that has NaOH (5 mg/ml of methanol). A third antiseptic solution was formed by dissolving chloroxylenol (200 mg/ml) and thymol (150 mg/ml) in an 85:15 solution of butyl acetate: methanol that has NaOH (5 mg/ml of methanol).

Eighteen-french silicone urinary catheters were dipped in one of the above coating solutions for 1 hour at 45° C. The catheters were allowed to dry overnight then rinsed. Some catheter segments were then incubated in urine for 1 week at 37° C.

The above results show broad spectrum activity of catheters coated with thymol and/or chloroxylenol. Except for *Pseudomonas aeruginosa*, the antimicrobial activity of coated catheters persists for at least one week. Although the combination of thymol and chloroxylenol is not synergistic, the use of this combination for coating may reduce the potential, although not very likely, emergence of resistance to these antiseptics.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

The present invention, therefore, is well adapted to carry out the objects and attain the ends and advantages mentioned as well as others inherent therein. While presently preferred embodiments of the invention are given for the purpose of disclosure, numerous changes in the details will readily suggest themselves to those skilled in the art and which are encompassed within the spirit of the invention and the scope of the appended claims.

What I claim is:

1. A method for impregnating non-metallic medical device with a combination of antiseptics comprising the steps of:

forming an antiseptic composition having an effective concentration to inhibit growth of bacterial and fungal organisms by dissolving a sufficient amount of said combination of antiseptics in an organic solvent and adding a penetrating agent to the antiseptic composition wherein said organic solvent is different from said penetrating agent; and applying the antiseptic composition to at least a portion of the medical device under conditions where the antiseptic composition permeates the medical device.

2. The method for impregnating a non-metallic medical device according to claim 1, wherein the organic solvent is methanol and the penetrating agent is butyl acetate.

3. The method for impregnating a non-metallic medical device according to claim 2, wherein the volume ratio of methanol to butyl acetate is 15:85.

4. The method for impregnating a non-metallic medical device according to claim 1, wherein the medical device is made from a material selected from the group consisting of rubber, plastic, silicone, polyurethane, polyethylene, polytetrafluoroethylene, and polyethylene tetraphthalate.

5. The method for impregnating a non-metallic medical device according to claim 1, wherein the medical device is a catheter selected from the group consisting of peripherally insertable central venous catheter, dialysis catheter, long term tunneled central venous catheter, peripheral venous catheter, short-term central venous catheter, arterial catheter, pulmonary artery Swan-Ganz catheter and urinary catheter.

TABLE 5

| Coating | S. epidermidis | | Enterococcus | | E. coli | | Pseudomonas | | Candida albicans | |
|---|---|---|---|---|---|---|---|---|---|---|
| | Initial | 1 week | Initial | 1 week | Initial | 1 week | Initial | 1 week | Initial | 1 week |
| Thymol | 38 | 30 | 28 | 17 | 35 | 28 | 11 | 0 | 60 | 38 |
| Chloroxylenol | 25 | 20 | 13 | 10 | 15 | 11 | 10 | 0 | 30 | 26 |
| Combination | 32 | 25 | 23 | 17 | 32 | 25 | 12 | 0 | 43 | 33 |

6. The method for impregnating a non-metallic medical device according to claim 1, wherein the medical device is a vascular graft.

7. The method for impregnating a non-metallic medical device according to claim 1, wherein the medical device is selected from the group consisting of vascular catheter port, wound drain tube, hydrocephalus shunt, peritoneal dialysis catheter, pacemaker capsule, artificial urinary sphincter, small joint replacement, temporary joint replacement, urinary dilator, urinary device, tissue bonding urinary device, penile prosthesis and heart valve.

8. The method for impregnating a non-metallic medical device according to claim 1, wherein the step of applying the antiseptic composition to the medical device comprises dipping the device in the composition for a period of between about 15 to 120 minutes, and removing the impregnated medical device from the antiseptic composition.

9. The method for impregnating a non-metallic medical device according to claim 8, wherein the medical device is dipped in the solution for a period of about 60 minutes.

10. The method for impregnating a non-metallic medical device according to any one of claims 1, 5, 6, or 7, wherein the combination of antiseptics is selected from the group of mixtures consisting of methylisothiazolone and thymol; chlorhexidine, methylisothiazolone and thymol; chlorhexidine, methylisothiazolone and α-terpineol; chloroxylenol and thymol; chlorhexidine and cetylpyridinium chloride; and chlorhexidine and chloroxylenol.

11. The method for impregnating a non-metallic medical device according to claim 4, wherein the non-metallic medical device is made from polyethylene tetraphthalate sealed with gelatin, collagen or albumin.

* * * * *